United States Patent [19]

Ruben

[11] 4,297,232
[45] Oct. 27, 1981

[54] GLYCOL-IODINE COMPOSITION AND METHOD OF PREPARATION

[76] Inventor: Samuel Ruben, 271 North Ave., New Rochelle, N.Y. 10801

[21] Appl. No.: 6,946

[22] Filed: Jan. 25, 1979

Related U.S. Application Data

[63] Continuation-in-part of Ser. No. 868,769, Jan. 12, 1978, abandoned, which is a continuation of Ser. No. 714,760, Aug. 16, 1976, abandoned.

[51] Int. Cl.³ .................... A61K 33/18; A01N 59/12
[52] U.S. Cl. ............................... 252/187 R; 252/308; 424/150; 424/343
[58] Field of Search ................. 252/309, 187 R; 424/150, 343

[56] References Cited

U.S. PATENT DOCUMENTS

| | | | |
|---|---|---|---|
| 1,013,913 | 1/1912 | Wemer | 424/150 |
| 1,580,400 | 4/1926 | Bommarito | 424/150 |
| 1,596,651 | 8/1926 | Bryant | 424/150 |
| 1,676,554 | 7/1928 | Hoopman | 424/150 |
| 1,719,523 | 7/1929 | Stephens | 424/150 |
| 1,767,667 | 6/1930 | Gray | 424/150 |
| 1,896,171 | 2/1933 | Harry | 424/150 |

OTHER PUBLICATIONS

Osol et al. "Solubility of Iodine in Glycol-Water Solutions", *J. Amer. Pharm. Assoc.* vol. 41, No. 12, Dec. 1952, pp. 634–637.
"glycol", *Hackh's Chemical Dictionary*, 4th Edition, McGraw Hill Book Company, NY (1972) pp. 302–303.

*Primary Examiner*—Deborah L. Kyle
*Attorney, Agent, or Firm*—David A. Jackson

[57] ABSTRACT

A composition comprising a glycol component including ethylene glycol and polymers thereof, and iodine, which composition is characterized by the absence of a spectroscopically identifiable complex between the glycol and iodine, and the absence of free iodine in mixture therewith. The composition of the present invention may be prepared in a wide variety of formulations and possesses therapeutic, environmental and industrial cleaning applications. Also disclosed is a method for the preparation of the composition employing an anhydrous environment and including heating the components to a temperature of about 180° C.

29 Claims, 2 Drawing Figures

GLYCOL-IODINE COMPOSITION AND METHOD OF PREPARATION

CROSS-REFERENCE TO RELATED APPLICATIONS

The present application is a continuation-in-part of copending Ser. No. 868,769, filed Jan. 12, 1978 now abandoned, which is in turn a continuation of U.S. Ser. No. 714,760, filed Aug. 16, 1976, now abandoned, all by the inventor herein.

BACKGROUND OF THE INVENTION

The present invention relates to organic iodine containing compositions, and more specifically to such compositions as release active iodine therefrom.

In my copending application Ser. No. 868,769, I discuss a hydrolyzable solution of ethylene glycol and iodine that responds negatively to iodine indicator testing, however, emits molecular iodine in the presence of or contact with an aqueous medium. The foregoing distinctions separate the iodine containing compound of my invention from the prior art wherein various alcoholiodine mixtures have been prepared, all of which indicate the presence of iodine upon testing. The preparation of the compositions of the present invention employs the mixture of ethylene glycol and iodine at temperatures on the order of 180° C.

In general, the preparation of iodine containing compositions is well documented. For example, U.S. Pat. No. 1,676,554 to Hoopman discloses a medicinal composition containing iodine in concert with a variety of glycerine. The composition is not prepared in the manner of my invention and, moreover, lacks all of the ingredients employed therein. Further, U.S. Pat. No. 1,596,651 to Bryant discloses an emollient composition including iodine, phenol, thymol and petrolatum oil and is accordingly distinguishable in the scope of ingredients and the emphasis on the employment of thymol to reduce the iodine content of the composition. U.S. Pat. No. 1,719,523 to Stevens discloses a composition comprising iodine and an alcohol. Patentee obtains a composition containing ethylene iodide which is clearly distinguishable from the composition of the present invention.

U.S. Pat. No. 1,580,400 to Bommarito relates to a composition comprising elementary iodine, potassium iodide, guaicol, distilled water and glycerine, for use in treatment of goiter by injection into the patient. In this composition, the glycerine serves as a solvent and is purported to reduce irritation incident to the injection process. The elementary iodine in Bommarito is stated to be the pure iodine found in the crystalline state, and the presence of this iodine, along with potassium iodide distinguishes Bommarito from the present invention.

U.S. Pat. No. 1,767,667 to Gray relates to a germicidal compound which employs the ingredients of zinc iodide, iodine in the resublimed form, menthol, glycerine, alcohol and water. Gray prepares his composition by a combination of the ingredients under low heat maintained below 40° C. By its definition, the composition of Gray is clearly distinguishable from that of the present invention.

U.S. Pat. No. 1,013,913 to Wemer relates to an iodine containing composition specifically comprised of iodine in mixture with glycerite of tannic acid. Wemer alleges that the crystalline iodine is in fact dissolved in the tannin and glycerine without changing the characteristics or properties thereof. Wemer is silent, however, with respect to the method of preparing his solution and, more importantly, does not suggest the application of heat in the manner taught by the present invention. Moreover, the composition of Wemer is distinguishable from that of the present invention in the employment of the tannic acid component.

Finally, U.S. Pat. No. 1,896,171 to Harry, cited against parent Ser. No. 714,760, relates to an iodine containing composition which employs iodine in mixture with glycerine and/or glycerol and tannic acid. A review of the Harry disclosure suggests that the tannic acid component is contemplated as a material ingredient (see Page 2, line 126-Page 3, line 6). Further, and more importantly, Harry discloses and claims that his composition contains free iodine which is in clear distinction to the teachings of the present invention.

In addition to the foregoing patent references, Applicant is aware of literature citations pertinent on the subject of the present invention. Specifically, an article by Osol and Pines relating to the solubility of iodine in glycol-water solutions is reported in the Journal of the American Pharmaceutical Association, at Volume 41, Page 634, wherein the authors review the solubility of iodine and various glycols, including ethylene and propylene glycols, along with the effect of adding water to solutions of iodine in the solvents. All of the investigations, however, were conducted at 25° C. and, as such, do not contemplate the preparation of Applicant's composition. Moreover, the relationship proposed by the authors to exist between the iodine and the respective glycols, comprising the existence of a complex analogous to triiodide ion, is distinguishable from the composition of the present invention, particularly as brought out hereinafter.

The most recent investigation of the interaction of iodine with various glycols is presented in a 1971 Ph.D. dissertation by G. D. Faile of Auburn University. The author conducted extensive ultraviolet spectroscopic investigations of various glycol-iodine systems, including that of ethylene glycol-iodine, all prepared at 25° C. and speculated that a complex relationship develops, that the author referred to as charge-transfer complexes. Specifically, ultraviolet spectroscopic analysis of ethylene glycol-iodine discloses a maximum absorption at 231 nanometers, which the author indicated is clearly indicative of the complex above noted. Faile, like the references noted earlier, however, does not appreciate the present invention and its specific method of preparation which employs a much higher temperature upon mixture, and for reasons to be elaborated hereinafter, further highlights by his work the unexpected properties of the composition of the present invention.

SUMMARY OF THE INVENTION

In accordance with the present invention, a composition is disclosed which comprises a glycol component including ethylene glycol, its polymers and mixtures thereof, and iodine, which composition is characterized by the absence of a spectroscopically identifiable complex between the glycol and iodine, and the absence of free iodine in solution. More particularly, the glycol may comprise ethylene glycol, diethylene glycol, triethylene glycol, polyethylene glycol and mixtures thereof, and the iodine content of the composition may vary and may include as much as 5 to 10% titratable iodine content. In a preferred embodiment, the composition of the present invention contains ethylene glycol and up to about 5% iodine, and preferably may contain from about 0.05% to 5% iodine.

The composition of the present invention may be prepared by a process which comprises adding to the glycol component the appropriate amount of iodine under agitation, heating the resulting mixture to about 180° C., followed by cooling the resulting solution to room temperature. In a preferred embodiment the method of the present invention is conducted in the total absence of all moisture, under substantially anhydrous conditions, and is thereafter maintained in the anhydrous state.

The composition of the present invention possesses a variety of utilities including employment as a medicinal aid, disinfectant and the like having utility in therapeutic, environmental and industrial maintenance applications, as well as any applications requiring the presence and activity of iodine. The composition operates in response to moisture to release free iodine in molecular form, while retaining the iodine in the absence of moisture in a state whereby the application of an iodine indicator to the composition yields negative results. Further, spectrograhpic analysis of the present composition, and in particular, observation of the ultraviolet spectrum yields the absence of a reaction indicating an iodine-glycol complex at the wavelength at which such complex is known to exhibit an absorption peak. Further, the composition of the present invention may be embodied in a wide variety of preparations including the placement within various dispersants, vehicles, emollients and the like depending upon the nature of the end utility desired.

Accordingly, it is a principal object of the present invention to provide an iodine containing composition which retains iodine in stable solution and releases said iodine in noncrystalline, molecular form upon contact with an aqueous environment.

It is a further object of the present invention to provide an iodine containing composition as aforesaid that facilitates the rapid release of molecular iodine and is not toxic in topical application to the human body.

It is a yet further object of the present invention to provide an iodine containing composition as aforesaid which exhibits favorably increased shelf stability.

It is a yet further object of the present invention to provide an iodine containing composition as aforesaid which exhibits unexpectedly improved antimicrobial activity.

It is a yet further object of the present invention to provide a method of preparing an iodine containing composition which yields a composition retaining iodine in stable solution.

Other objects and advantages will become apparent to those skilled in the art from a review of the ensuing description which proceeds with reference to the following accompanying figures.

DETAILED DESCRIPTION OF THE INVENTION

Figure 1:
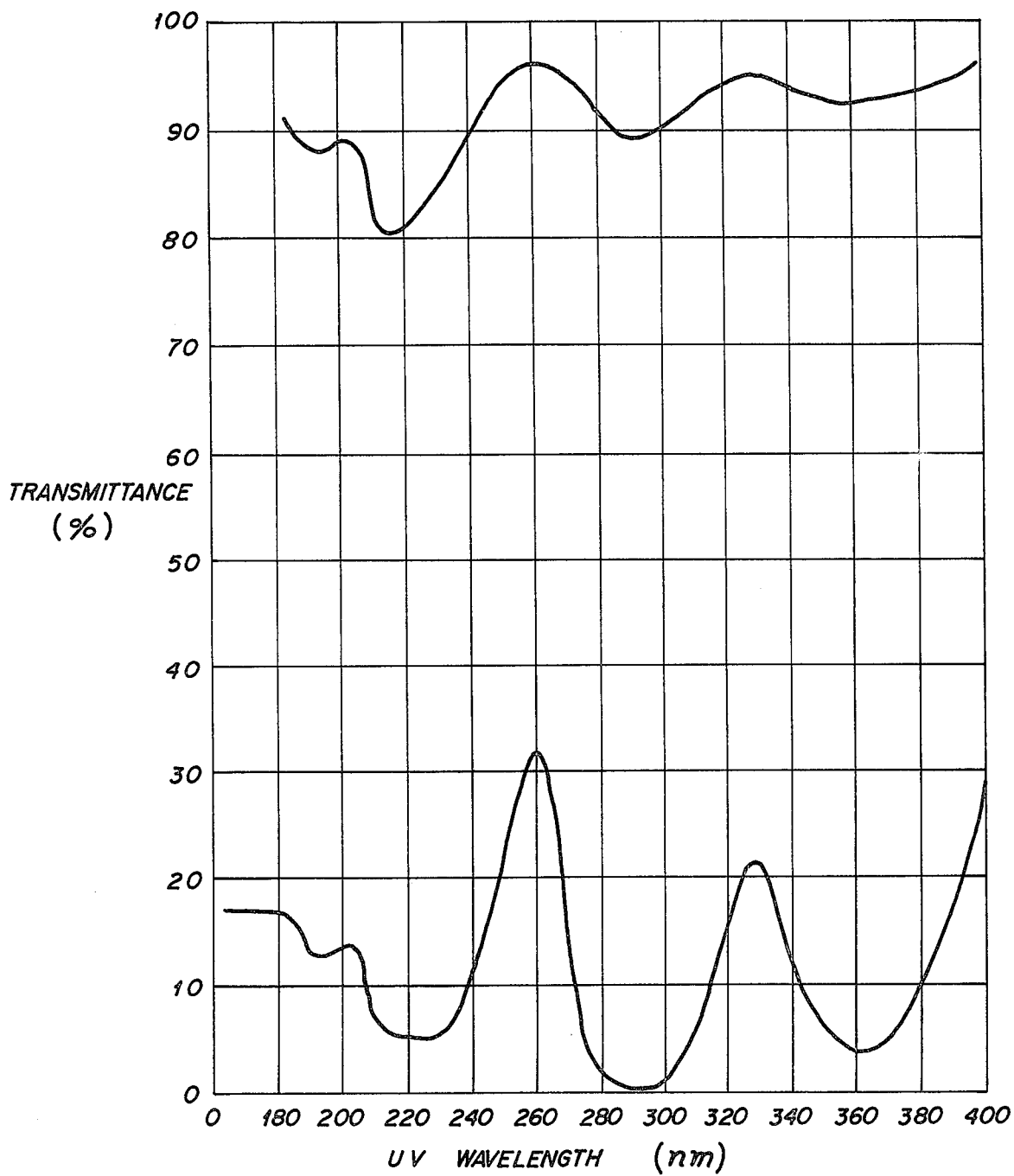
FIG. 1 comprises an ultraviolet spectrograph of the mixture of ethylene glycol and iodine in accordance with the prior art.

In accordance with the present invention the foregoing objects and advantages are readily attained.

The present invention comprises a composition comprising a glycol component comprising ethylene glycol, its polymers and mixtures thereof, and iodine, which composition is characterized by the absence of a spectroscopically identifiable complex between the glycol and iodine, and the absence of free iodine therein. More particularly, the glycol component of the present invention may comprise a compound selected from the group consisting of ethylene glycol, diethylene glycol, triethylene glycol, polyethylene glycol, and mixtures thereof, and in a preferred embodiment, the glycol component comprises ethylene glycol.

The present composition is distinguishable from the prior art by its negative response to ultraviolet spectrographic analysis respecting the presence of a glycol-iodine complex as had been reported in the prior art in the doctoral thesis by Faile, discussed earlier. Further, when prepared in accordance with the method of the present invention, the present compositions respond negatively to tests for free iodine in solution, suggesting that the iodine is maintained in some form of complex other than the conventional alcohol-iodine charge transfer complex suggested in the literature. This form of composition appears to ensure the substantially complete retention of iodine in solution over extended periods of time, thereby conferring a favorably extended shelf life. Further, in addition to the ability of the present composition to effectively sequester iodine in a distinctive complex relationship, the composition is capable of releasing non-crystalline, molecular iodine from solution upon immediate contact with an aqueous environment, including moisture. Finally, the present composition has been found to possess improved microbiocidal activity with reduced causticity to the body which is accordingly desirable in a wide variety of medicinal applications.

As noted earlier and in my copending applications, the composition of the present invention appears to comprise a unique mixture which may be characterized as a reaction product, in that the compounds contained therein interact in some fashion after their combination in accordance with the present method. Specifically, the iodine component appears unavailable in the free state and is, moreover, not seen to complex in the conventional manner with the alcohol moities of the glycol. Earlier discussion focusing on the thesis of Faile indicated that the author experimented with various iodine-alcohol systems, in particular the system comprising ethylene glycol and iodine, to determine the interaction believed to exist between alcohol substituents and iodine. The author proceeded to conduct tests comprising ultraviolet spectral analysis and determined that certain absorption bands observed reflected the existence of a complex between the alcohol and iodine, referred by the author as a charge-transfer complex. Applicant has undertaken to conduct comparative testing to determine whether the composition of the present invention possesses a structure of the type characterized by Faile, or whether some different structure exists. The comparative experiments are set forth below.

EXPERIMENT I

A composition comprising ethylene glycol dried in contact with magnesium sulfate and subsequently distilled was then placed in an aqueous solution to exhibit up to 1.0 mole fraction concentration of alcohol. One hundred milliliters of this solution was then made $10^{-4}$ M in $HClO_4$ to suppress triiodide formation. Three milliliters of the resulting stock solution were then placed in the sample cell of an ultraviolet spectrophotometer to observe the ultraviolet spectrum thereof. To the sample cell containing the stock solution, three crystals of resublimed iodine were added and stirred. The original stock solution was located in a reference compartment and a spectrum was then run. The foregoing procedure was followed in accordance with the experiments conducted by Faile, supra., as set forth on pages 11-15. The resulting spectrum, presented in FIG. 1, indicates that, as observed by the author, an absorption peak occurs in the area of 231 nanometers which suggests that a charge-transfer complex exists between the alcohol substituents of the ethylene glycol and the iodine.

EXPERIMENT II

Figure 2:
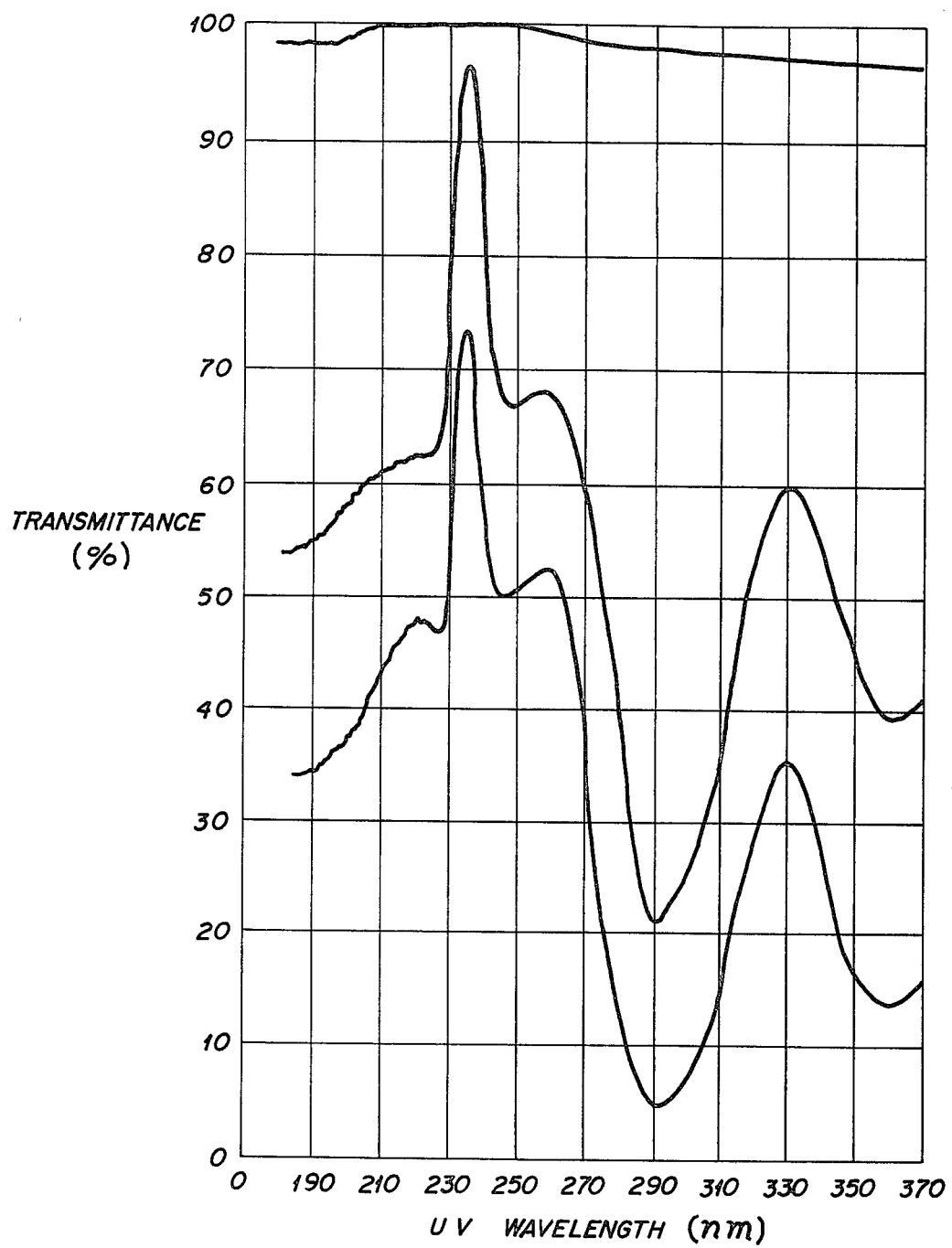
FIG. 2 is an ultraviolet spectrograph obtained from analysis of the composition of the present invention.

By comparison the composition of the present invention was prepared by reacting the ethylene glycol and iodine components in the absence of water in a commercial reaction vessel by heating the components to a temperature of about 160° C., followed by cooling the resulting solution to room temperature while maintaining the solution in an air and moisture exclusive environment. A sample of the solution was then placed in the ultraviolet spectrophotometer and, as a reference, the ethylene glycol prepared in accordance with Faile was employed. The spectrum observed shows the absence of absorption in the areas noted by the author, and, particularly, indicated a marked increase in transmittance in the area of 230-240 nanometers. As can be seen in FIG. 2, two spectra were run simultaneously each comprising production preparations of the composition of the present invention containing 3% iodine as well as the comparative ethylene glycol reference sample. From the above, it is apparent that the exact structure of the composition of the present invention indeed varies from that both known and expected in the prior art as represented by Faile.

In addition to the structural distinction discussed above, the foregoing tests further established that no free iodine is present in the solutions prepared in accordance with the present invention, particularly, as noted by Faile on page 67 thereof, the appearance of an absorption band at 203 nanometers was indicative of the existence of free iodine in a glycol solution. Referring again to FIG. 2, however, no such absorption appears to exist, as the transmittance of the sample is seen to increase at that wavelength. The above tests are therefore believed to establish both the absence of a complex existing between the alcohol substituent of the glycol component and iodine, and the absence of free iodine from the solution comprising the composition of the present invention.

As indicated earlier, the composition of the present invention may be prepared in a wide variety of iodine concentrations to suit the end utility for which the composition is intended. Thus, the iodine content of the composition of the present invention may vary up to the saturation point of iodine in the glycol component, and may, for example, extend up to 5-10% iodine. More particularly, the compositions containing on the order of about 5% iodine may be prepared for use in certain medicinal and industrial applications, and in a further embodiment such compositions may contain from 0.05-5% iodine.

In accordance with the present invention, a method of preparation is also disclosed which is believed to contribute to the distinctive properties of the present composition. More particularly, an important element of the method of the present invention is that the glycol and iodine components are heated with agitation to a temperature on the order of 180° C. Once this temperature is reached, the completed product is removed from the heat source and allowed to cool to room temperature. In a preferred embodiment, the glycol component is provided in substantially anhydrous condition and may be prepared, for example, by exposure to magnesium sulfate to remove all moisture therefrom. The glycol is then retained in substantially anhydrous conditions, either by maintenance in an inert atmosphere or vacuum, and the appropriate quantity of iodine in crystal form is added thereto and the resulting mixture agitated to dissolve the iodine crystals. The resulting solution is then brought to the aforementioned temperature while maintained under anhydrous conditions, and subsequently cooled to room temperature to form the completed reaction product.

An important feature of the method of the present invention is that the composition is heated to a temperature of approximately 180° C. Applicant notes that, whereas compositions containing higher alcohols such as glycerol and the like form an unhydrolyzable compound by reaction within this temperature range, the composition of the invention is readily hydrolyzable upon contact with an aqueous environment to yield free iodine in molecular form. More particularly, the method of the present invention may be practiced at a temperature ranging from about 140° C. to about 180° C., and in a preferred embodiment, a reaction temperature of 160° C. may be employed.

A further feature of the method comprises the employment of anhydrous reaction conditions to produce a composition substantially free from water. The employment of anhydrous reaction conditions has been unexpectedly found to add greater stability to the resulting composition, as it assists in the retention of iodine in combination with the glycol such that iodine indicator tests showed negative results and the absence of free iodine from solution. Though the establishment and maintenance of anhydrous reaction conditions is preferred, it is not mandatory, as the composition of the present invention may be prepared under conditions permitting exposure to air and consequent moisture while nonetheless resulting in a composition possessing all of the aforementioned properties. Accordingly, the invention is not to be construed as limited to the employment of anhydrous conditions, but such conditions are to be considered as representative of a best mode of practicing the invention.

As indicated earlier, the composition of the present invention may be embodied in a wide variety of applications and, accordingly, may be formulated with various additives, dispersants, carriers and the like to facilitate its employment therein. Specifically, the present composition has been found to possess substantial antibacterial and antimicrobial efficacy and, in the instance where a topical preparation for use with the human body is contemplated, the composition may be mixed with an appropriate dispersant such as propylene glycol for application in liquid form. Preferably, such a mixture may, for example, be prepared by combining one part by volume of the composition of the present invention with three parts by volume of propylene glycol.

In the instance where an ointment or salve is desired, the composition of the present invention may be admixed with a suitable quantity of a bodying agent or carrier such as mannitol or a polyethylene glycol having a higher molecular weight on the order of 6000, in proportions which may vary between the components to provide a preparation varying in consistency from that of a cream to that of a thick paste. Further, other materials may be employed which serve to provide appropriate media for presentation of the present composition depending upon the utility desired. Thus, for example, the composition of the present invention may also be employed as a liquid additive in such environments as fish breeding waters, and in water purification and dental sterilization, as well as hard surface cleaning applications. In each instance, the composition may be employed individually or in combination with appropriate additives.

The scope of the present invention is illustrated with reference to the examples, which proceed below.

EXAMPLE 1

Two grams of iodine crystals were added to 100 grams of ethylene glycol under agitation in a 500 milliliter beaker at room temperature. The ethylene glycol-iodine mixture was then heated to a temperature of approximately 160° C. with continued agitation, and upon reaching that temperature was immediately removed from the heat source and permitted to cool to room temperature. The beaker was maintained tightly covered and no further agitation was applied during the cooling period.

EXAMPLE 2

9.0 grams of iodine were placed in a loosely covered 500 milliliter beaker at room temperature, and 450 grams of ethylene glycol were then added thereto under agitation. The ethylene glycol-iodine mixture was then heated to a temperature approaching 160° C. with continued agitation. Upon reaching 160° C., the beaker containing the composition was immediately removed from the heat source and the solution was allowed to cool slowly to room temperature under tight cover and without further agitation.

One part by volume of the above composition was then mixed at room temperature with three parts by volume of propylene glycol. The resulting mixture was then tested for free iodine by dipping of starch indicator paper into a portion thereof. The starch indicator paper showed no reaction indicating the absence of free iodine from the solution.

EXAMPLE 3

This example illustrates the preparation of the composition of the present invention wherein the glycol component comprises diethylene glycol. Accordingly, 5.37 grams of iodine was placed in a loosely covered 250 milliliter Erlenmeyer flask, and 263.0 grams of diethylene glycol was then added thereto under agitation. The resulting mixture, which possessed an iodine content of approximately 2% by weight, was then heated to a temperature approaching 160° C. with continued agitation. Upon reaching 160° C. the flask was removed from the heat source and permitted to cool slowly to room temperature under tight cover and without further agitation. The resulting composition was then titrated with 0.1 N $Na_2S_2O_3$ standard solution and found to contain 1.35% available iodine.

The foregoing composition compares favorably with a comparable composition prepared with monoethylene glycol which, when titrated, yielded 1.30% available iodine. Further, in all other respects, the composition of Example 3 responded in like manner to those of Examples 1 and 2.

EXAMPLE 4

The composition of the present invention was prepared wherein the glycol component comprises polyethylene glycol. Specifically, 3 grams of iodine were placed in a loosely covered 500 milliliter container at room temperature, and 97 grams of a polyethylene glycol having a molecular weight of 400 was then added thereto under agitation. The glycol-iodine mixture was then heated to a temperarture approaching 160° C. with continued agitation, after which the container was then removed from the heat source and the solution permitted to cool slowly to room temperature under tight cover and without further agitation. The above product was then titrated with 0.1 N $Na_2S_2O_3$ standard solution and was found to contain approximately 1.915% available iodine. The composition as prepared responded negatively to tests for available iodine, however, upon mixture with water, responded positively to iodine indicator testing.

The composition of the present invention is characterized by its ability to release molecular iodine on contact with an aqueous medium and, accordingly, is useful in instances where oxidation or the localized effect of iodine on organic compounds is desirable. Moreover, the composition possesses antimicrobial specificity which renders it useful as an antiseptic and disinfectant in industrial uses. The composition is likewise nontoxic to living tissue and is accordingly acceptable for use as a topically applied medicinal preparation.

Certain tests were conducted to establish the foregoing utilities, which tests are presented below.

EXPERIMENT 3

The composition of the present invention was prepared with a free iodine titration of 0.3% and was diluted in trypticase soy broth (TSB) in a series of concentrations ranging from 0.0003–0.075% free $I_2$. The respective growth media prepared were then inoculated with the following organisms which were then grown at 35° C. for 16–18 hours; *Staphylococcus aureus* ATCC #6538, *Staphylococcus aureus*-Gregg strain, *Staphylococcus albus* 914-4-1A, *Pseudomonas cepacia* 153, *Sarcina lutea* ATCC #9341RR, *Escherichia coli* ATCC #10536, *Pseudomonas aeruginosa* 568-18-1A and *Enterobacter cloacae* 603-1-1B. Inoculation was accomplished by adding 0.05 milliliters (1 drop) of the overnight broth culture to 10 milliliters of antimicrobial agent in TSB. Transfer tubes, used to determine cidal endpoints for the titrated compounds, were prepared by adding the neutralizers, Tween 80 ® (0.5%), lecithin (0.07%), and sodium thiosulfate (1%), to TSB.

The inoculated tubes containing the dilutions of test compounds were incubated for 48 hours at 35° C.; the presence of growth (+) for each tube was recorded. From the tube showing no growth (−), 1.0 milliliters of solution was transferred to 10 milliliters of neutralization broth, and the tubes containing the neutralization broth were then incubated for 48 hours at 35° C. The absence of growth in these tubes determined the cidal endpoint for each sample. The results of these tests are set forth in Table 3.

TABLE 3

CIDAL ACTIVITY
CIDAL ACTIVITY OF eMDee IODO COMPOUND

| Organisms | Test Concentration (expressed as % free $I_2$) | | | | | | | |
|---|---|---|---|---|---|---|---|---|
| | 0.0003 | 0.003 | 0.03 | 0.033 | 0.038 | 0.050 | 0.060 | 0.075 |
| Staphylococcus aureus ATCC #6538 | + | + | − | − | − | − | − | − |
| Staphylococcus aureus Gregg strain | + | + | − | − | − | − | − | − |
| Staphylococcus albus 914-4-1A | + | + | + | − | − | − | − | − |
| Pseudomonas cepacia 153 | + | + | + | − | − | − | − | − |
| Sarcina lutea ATCC #9341RR | + | + | − | − | − | − | − | − |
| Escherichia coli ATCC #10536 | + | + | + | + | + | − | − | − |
| Pseudomonas aeruginosa 568-18-1A | + | + | + | + | + | − | − | − |
| Enterobacter cloacae 603-1-1B | + | + | + | + | + | − | − | − |

+ = growth
− = no growth

From the tests tabulated above, it was determined that the composition of the present invention required a concentration of 0.03% free iodine to prove cidal for gram-positive bacteria, and a concentration of 0.05% free iodine to be cidal for gram negative bacteria. Thus, the cidal activity of the composition of the present invention is clearly in evidence.

EXPERIMENT 4

The composition of the present invention was tested for dermal toxicity in accordance with the Hazardous Substances Labeling Act Regulations, Part 191, Chapter 1, Title 21, Code of Federal Regulations, Paragraph 191.10 by application of a dosage level of 2.2 grams/kilogram contained on a gauze pad to the bare skin of six rabbit subjects, and the retention of the pads in position for measured intervals of 24 and 72 hours. The results of the tests were that no deaths were caused by the composition, and the composition was thereby determined to be dermally nontoxic.

EXPERIMENT 5

Further toxicity studies were conducted comprising eye irritation testing. Accordingly, 0.1 milliliter samples of the composition tested in Experiment 4 were applied to the eyes of albino rabbits in accordance with the method set forth in the Hazardous Substances Labeling Act Regulations, Part 191, Chapter 1, Title 21, Code of Federal Regulations, Paragraph 191.12. Specifically, the composition was applied to one of the rabbits' eyes with the other eye retained as a control. The eyes are subsequently examined and the rate of ocular reaction noted daily for a total of 7 days. Six rabbit subjects were employed for the tests and the results thereof are set forth in Table 5, below:

TABLE 5

EYE IRRITATION TESTING

| Findings: Antiseptic Compound | DAYS | | | | | | |
|---|---|---|---|---|---|---|---|
| | 1 | 2 | 3 | 4 | 5 | 6 | 7 |
| Rabbit # 1 | | | | | | | |
| I. Cornea | | | | | | | |
| A. Opacity | 0 | 0 | 0 | 0 | 0 | 0 | 0 |
| B. Area | 0 | 0 | 0 | 0 | 0 | 0 | 0 |
| A × B × 5 | | | | | | | |
| II. Iris | | | | | | | |
| A. Values × 5 | 0 | 0 | 0 | 0 | 0 | 0 | 0 |
| III. Conjunctivae | | | | | | | |
| A. Redness | 0 | 0 | 0 | 0 | 0 | 0 | 0 |
| B. Chemosis | 0 | 0 | 0 | 0 | 0 | 0 | 0 |
| 1 C. Discharge | 0 | 0 | 0 | 0 | 0 | 0 | 0 |
| (A + B + C) × 2 Total | 0 | 0 | 0 | 0 | 0 | 0 | 0 |
| Rabbit # 2 | | | | | | | |
| I. Cornea | | | | | | | |
| A. Opacity | 0 | 0 | 0 | 0 | 0 | 0 | 0 |
| B. Area | 0 | 0 | 0 | 0 | 0 | 0 | 0 |
| A × B × 5 | | | | | | | |
| II. Iris | | | | | | | |
| A. Values × 5 | 0 | 0 | 0 | 0 | 0 | 0 | 0 |
| III. Conjunctivae | | | | | | | |
| A. Redness | 0 | 0 | 0 | 0 | 0 | 0 | 0 |
| B. Chemosis | 0 | 0 | 0 | 0 | 0 | 0 | 0 |
| C. Discharge | 0 | 0 | 0 | 0 | 0 | 0 | 0 |
| (A + B + C) × 2 Total | 0 | 0 | 0 | 0 | 0 | 0 | 0 |
| Rabbit # 3 | | | | | | | |
| I. Cornea | | | | | | | |

TABLE 5-continued

EYE IRRITATION TESTING

| Findings: Antiseptic Compound | DAYS | | | | | | |
|---|---|---|---|---|---|---|---|
| | 1 | 2 | 3 | 4 | 5 | 6 | 7 |
| A. Opacity | 0 | 0 | 0 | 0 | 0 | 0 | 0 |
| B. Area | 0 | 0 | 0 | 0 | 0 | 0 | 0 |
| A × B × 5 | | | | | | | |
| II. Iris | | | | | | | |
| A. Values × 5 | 0 | 0 | 0 | 0 | 0 | 0 | 0 |
| III. Conjunctivae | | | | | | | |
| A. Redness | 0 | 0 | 0 | 0 | 0 | 0 | 0 |
| B. Chemosis | 0 | 0 | 0 | 0 | 0 | 0 | 0 |
| C. Discharge | 0 | 0 | 0 | 0 | 0 | 0 | 0 |
| (A + B + C) × 2 Total | 0 | 0 | 0 | 0 | 0 | 0 | 0 |
| Rabbit # 4 | | | | | | | |
| I. Cornea | | | | | | | |
| A. Opacity | 0 | 0 | 0 | 0 | 0 | 0 | 0 |
| B. Area | 0 | 0 | 0 | 0 | 0 | 0 | 0 |
| A × B × 5 | | | | | | | |
| II. Iris | | | | | | | |
| A. Values × 5 | 0 | 0 | 0 | 0 | 0 | 0 | 0 |
| III. Conjunctivae | | | | | | | |
| A. Redness | 0 | 0 | 0 | 0 | 0 | 0 | 0 |
| B. Chemosis | 0 | 0 | 0 | 0 | 0 | 0 | 0 |
| C. Discharge | 0 | 0 | 0 | 0 | 0 | 0 | 0 |
| (A + B + C × 2 Total | 0 | 0 | 0 | 0 | 0 | 0 | 0 |
| Rabbit # 5 | | | | | | | |
| I. Cornea | | | | | | | |
| A. Opacity | 0 | 0 | 0 | 0 | 0 | 0 | 0 |
| B. Area | 0 | 0 | 0 | 0 | 0 | 0 | 0 |
| A × B × 5 | | | | | | | |
| II. Iris | | | | | | | |
| A. Values × 5 | 0 | 0 | 0 | 0 | 0 | 0 | 0 |
| III. Conjunctivae | | | | | | | |
| A. Redness | 0 | 0 | 0 | 0 | 0 | 0 | 0 |
| B. Chemosis | 0 | 0 | 0 | 0 | 0 | 0 | 0 |
| C. Discharge | 0 | 0 | 0 | 0 | 0 | 0 | 0 |
| (A + B + C) × 2 Total | 0 | 0 | 0 | 0 | 0 | 0 | 0 |
| Rabbit # 6 | | | | | | | |
| I. Cornea | | | | | | | |
| A. Opacity | 0 | 0 | 0 | 0 | 0 | 0 | 0 |
| B. Area | 0 | 0 | 0 | 0 | 0 | 0 | 0 |
| A × B × 5 | | | | | | | |
| II. Iris | | | | | | | |
| A. Values × 5 | 0 | 0 | 0 | 0 | 0 | 0 | 0 |
| III. Conjunctivae | | | | | | | |
| A. Redness | 0 | 0 | 0 | 0 | 0 | 0 | 0 |
| B. Chemosis | 0 | 0 | 0 | 0 | 0 | 0 | 0 |
| C. Discharge | 0 | 0 | 0 | 0 | 0 | 0 | 0 |
| (A + B + C) × 2 Total | 0 | 0 | 0 | 0 | 0 | 0 | 0 |

From the above tests, it is apparent that the composition of the present invention produced no irritation in rabbit eyes and as such may be considered non-irritating.

The foregoing data suggests that the composition of the present invention possesses utility in medicinal and general industrial situations where bacteriocidal properties are desirable. Naturally, the composition as indicated earlier is capable of employment in applications of varying utility in addition to those specifically illustrated above, and the scope of the invention is accordingly not limited thereto.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

I claim:

1. A composition consisting essentially of a glycol component selected from the group consisting of ethylene glycol, the polymers thereof and mixtures thereof, and iodine, said iodine present in an amount up to the saturation point of said iodine in said glycol component, said composition characterized by the absence of a spectroscopically identifiable complex between said glycol component and said iodine, and the absence of free iodine therein.

2. The composition of claim 1 wherein said glycol component is selected from the group consisting of ethylene glycol, diethylene glycol, triethylene glycol, polyethylene glycol and mixtures thereof.

3. The composition of claim 1 wherein said glycol component comprises ethylene glycol.

4. The composition of claim 1 wherein said iodine is present in an amount equivalent to up to about 10% titratable free $I_2$.

5. The composition of claim 4 wherein said iodine is present in an amount equivalent to up to about 5% titratable $I_2$.

6. The composition of claim 5 wherein said iodine content ranges from about 0.05 to about 5%.

7. The composition of claim 6 wherein said iodine content is approximately 1.5%.

8. The composition of claim 1 wherein said composition is maintained in anhydrous condition.

9. The composition of claim 1 further including an additive selected from the group consisting of dispersants, carriers, bodying agents, perfumes, emollients, and mixtures thereof.

10. The composition of claim 9 wherein said additive comprises propylene glycol.

11. The composition of claim 10 wherein said proplyene glycol is combined with said composition in the ratio 1 part of said composition to 3 parts of said propylene glycol.

12. The composition of claim 9 wherein said additive comprises mannitol.

13. The composition of claim 9 wherein said additive comprises polyethylene glycol having a molecular weight of about 6000.

14. An method for preparing an iodine containing composition having no free iodine present therein which comprises forming a mixture consisting essentially of a quantity of glycol component selected from the group consisting of ethylene glycol, its polymers and mixtures thereof, and a quantity of iodine ranging in amount up to the saturation point of said iodine in said glycol component, heating said mixture to temperature from about 140° C. to about 180° C., and thereafter cooling said mixture to room temperature.

15. The method of claim 14 wherein said temperature ranges up to about 160° C.

16. The method of claim 14 wherein said glycol component and said iodine are agitated during mixing and heating.

17. The method of claim 14 wherein said glycol component, said iodine and said mixture are maintained in substantially anhydrous conditions.

18. The method of claim 14 wherein said glycol component is selected from the group consisting of ethylene glycol, diethylene glycol, triethylene glycol, polyethylene glycol and mixtures thereof.

19. The method of claim 14 wherein said glycol component comprises ethylene glycol.

20. The method of claim 14 wherein said iodine and said glycol component are present in amounts sufficient to prepare said mixture to possess an available iodine content equivalent to up to about 10% titratable $I_2$.

21. The method of claim 20 wherein said iodine content may range up to about 5%.

22. The method of claim 21 wherein said iodine content may range from about 0.05 to about 5%.

23. A composition comprising the reaction product formed from heating a mixture consisting essentially of a glycol component selected from the group consisting of ethylene glycol, its polymers and mixtures thereof, and iodine, said iodine present in an amount up to the saturation point of said iodine in said glycol component, to a temperature of up to about 180° C.

24. The composition of claim 23 wherein said temperature ranges from about 140° C. to about 180° C.

25. The composition of claim 23 wherein said temperature ranges up to about 160° C.

26. The composition of claim 23 wherein said glycol component is selected from the group consisting of ethylene glycol, diethylene glycol, triethylene glycol, polyethylene glycol and mixtures thereof.

27. The composition of claim 23 wherein said glycol component comprises ethylene glycol.

28. The composition of claim 23 wherein said iodine is present in an amount equivalent to up to about 10% titratable $I_2$.

29. The composition of claim 23 wherein said reaction product is prepared and maintained under substantially anhydrous conditions.

* * * * *